(12) United States Patent
Yared et al.

(10) Patent No.: US 8,492,734 B2
(45) Date of Patent: Jul. 23, 2013

(54) IMAGING SYSTEMS FEATURING WAVEGUIDING COMPENSATION

(75) Inventors: Wael I. Yared, Lexington, MA (US); Pouyan Mohajerani, Smyrna, GA (US); Joshua Kempner, Reading, MA (US)

(73) Assignee: VisEn Medical, Inc., Waltham, MA (US)

( * ) Notice: Subject to any disclaimer, the term of this patent is extended or adjusted under 35 U.S.C. 154(b) by 440 days.

(21) Appl. No.: 12/738,615

(22) PCT Filed: Jun. 3, 2008

(86) PCT No.: PCT/US2008/065648
§ 371 (c)(1),
(2), (4) Date: Nov. 18, 2010

(87) PCT Pub. No.: WO2009/055095
PCT Pub. Date: Apr. 30, 2009

(65) Prior Publication Data
US 2011/0049384 A1    Mar. 3, 2011

Related U.S. Application Data

(60) Provisional application No. 60/981,316, filed on Oct. 19, 2007.

(51) Int. Cl.
*G01N 21/64* (2006.01)
*G06T 7/00* (2006.01)
(52) U.S. Cl.
USPC ............... 250/458.1; 250/461.2; 382/128

(58) Field of Classification Search
USPC ..... 250/458.1–461.2; 382/128, 131; 600/425, 600/407, 476
See application file for complete search history.

(56) References Cited

U.S. PATENT DOCUMENTS 6,563,122 B1 * 5/2003 Ledeker et al. ............ 250/458.1
2007/0238957 A1 * 10/2007 Yared ........................... 600/407

OTHER PUBLICATIONS

Soubret et al. "Accuracy of Fluorescent Tomography in the Presence of Heterogeneities: Study of the Normalized Born Ratio," IEEE Trans. Med. Imag. (24) 10, Oct. 2005, p. 1377-1386.*

* cited by examiner

*Primary Examiner* — Casey Bryant
(74) *Attorney, Agent, or Firm* — Choate, Hall & Stewart, LLP

(57) ABSTRACT

In certain embodiments, the invention relates to systems and methods for altering an image to compensate for variation in one or more physical and/or supervenient properties (e.g., optical absorption and/or scattering) in heterogeneous, diffuse tissue, thereby attenuating the effects of tissue waveguiding. The methods enable the proper identification of emission image regions that evidence waveguiding of electromagnetic radiation, and enables compensation of emission images for such waveguiding. The methods preserve the depth localization accuracy of the FMT approach and improve optical reconstruction in the targeted areas while eliminating spurious components of fluorescence from the acquired data set. Calibration methods for probe concentration mapping are also presented.

19 Claims, 10 Drawing Sheets

IMAGING SYSTEMS FEATURING WAVEGUIDING COMPENSATION

RELATED APPLICATION

This application is a national stage of International (PCT) Patent Application Serial No. PCT/US2008/065648, filed Jun. 3, 2008, and published under PCT Article 21(2) in English, which claims priority to and the benefit of U.S. provisional patent application Ser. No. 60/981,316, filed Oct. 19, 2007, the disclosure of which is incorporated herein by reference in its entirety.

GOVERNMENT RIGHTS

The invention was supported, in whole or in part, by grant 1 R44 ES012699-01 from the National Institute of Environmental Health Sciences. The Government has certain rights in the invention.

FIELD OF THE INVENTION

The invention relates generally to in vivo imaging systems and methods. More particularly, in certain embodiments, the invention relates to systems and methods for altering an image to compensate for variation in one or more physical and/or supervenient properties (e.g., optical absorption and/or scattering) in heterogeneous, diffuse tissue, thereby attenuating the effects of tissue waveguiding.

BACKGROUND OF THE INVENTION

Objects imaged using electromagnetic radiation, including visible light, infrared light, x-rays, gamma rays and radio frequency waves, can exhibit significant heterogeneity. For example, in the case of objects imaged with light, this heterogeneity manifests itself as microscopic- as well as macroscopic-level changes in optical properties, for example, variation in the coefficient of optical absorption or the coefficient of scattering throughout the object. Macroscopic-level changes in the coefficient of optical absorption have significant impact on the propagation of light through and around such areas. In particular, light tends to tunnel, or waveguide, through areas exhibiting lower optical absorption, thus taking the path of least resistance. Similar waveguiding effects can be observed with other forms of electromagnetic radiation propagating through heterogeneous media.

When acquiring a image of a diffuse heterogeneous object, such as animals, humans, and/or any biological tissue for example, using electromagnetic radiation, the object regions that the radiation has propagated to because of any waveguiding effects will appear disproportionately intense to the detector or detectors measuring the electromagnetic radiation. These regions of high apparent intensity, sometimes called "hot spots," can give rise to regions of false or exaggerated intensity in the two dimensional images or in three dimensional tomographic image reconstruction of the object. This can cause misleading or false attribution of the electromagnetic radiation signal, and/or agent or probe distribution to such object regions, when such object regions might have very little or no agent or probe (including endogenous agents and exogenous agents). This waveguiding phenomenon holds for any electromagnetic radiation propagating through a heterogeneous object, regardless of whether or not there are exogenous or endogenous agents. The proportion or amount of agent/probe as well as its location would be inaccurate due to the waveguiding effects of electromagnetic radiation, causing artifacts in two dimensional images and tomographic images. Regions of objects more absorbent to electromagnetic radiation might cause waveguiding or tunneling into regions of less absorption, creating inaccurate or erroneous attribution of radiative signal. For example, in biological tissue such as the heart region of a mammal, cardiac muscle is more absorbant than skin or subcutaneous fat. Radiation, such as (but not limited to) light, traveling through the tissue would tend to tunnel, or waveguide, into regions of lower relative absorbance, such as the skin. This would give rise to inaccurate and false attribution of radiation concentrated in regions vulnerable to waveguided radiation such as skin folds or other thin tissue.

Thus, there is a need for systems and methods for compensating for the effects of waveguiding. This need is especially urgent for in vivo optical imaging of heterogeneous diffuse objects such as animals, humans and biological tissue.

SUMMARY OF THE INVENTION

The invention relates to systems and methods for identifying waveguiding of electromagnetic radiation in heterogeneous diffuse objects and compensating for such effects in image display, analysis and reconstruction. For example, in various embodiments, the invention provides systems and methods for detecting regions of (and/or the effects of) electromagnetic radiation wave guiding in heterogeneous diffuse objects, estimating the component of radiation signal from these regions that is attributable to waveguiding effects from neighboring regions, and accounting for this component in image analysis, display and tomographic reconstruction These methods yield a more accurate depiction of the localization and distribution of the signal in the object, including quantification and distribution of signals, reporters and/or agents (e.g., contrast agents or probes) in such objects than can be achieved by imaging techniques that do not compensate for any waveguiding effects.

In accordance with embodiments of the present invention, waveguiding compensation systems and methods are described herein. These systems and methods can be fully parameterized to accommodate different imaging settings optimized for a variety of target objects and regions and a variety of different agents or probes. In certain embodiments, the invention provides such systems and corrected image analysis methods for use in biological research, as well as in preclinical and/or clinical settings. For examples, in certain embodiments, the present invention provides corrected imaging systems and methods that can optionally be used with one or more imaging agents or probes for in vivo molecular imaging.

For example, fluorescence molecular tomography (FMT) systems and methods, as well as other probe/marker/agent-based tomographic systems and methods, are presented herein that feature two steps that can be performed separately or together to compensate for waveguiding in resulting tomographic images—(i) obtaining an estimated probe emission image based wholly or in part on an excitation (intrinsic) image and altering the detected probe emission image accordingly (e.g., by subtracting the estimated emission image from the detected emission image); and/or (ii) determining a coincidence mask from the excitation (intrinsic) image and the detected emission image and altering the detected emission image accordingly. A plurality of emission images are altered in this matter, and the altered images are used in tomographic reconstruction.

In one aspect, the invention relates to a method for compensating an image for waveguiding effects, the method comprising: (a) detecting electromagnetic radiation emanating from a heterogeneous diffuse object, thereby acquiring an image; and (b) altering said image to reduce or eliminate an effect of physical (and/or supervenient) property variation in said heterogeneous diffuse object.

In certain embodiments, any one or more of the following may hold: step (a) comprises detecting electromagnetic radiation transmitted through said heterogeneous diffuse object; said heterogeneous diffuse object comprises a biological object; said biological object is a member selected from the group consisting of an animal, a mammal, a human, and a plant; said biological object comprises a biological tissue; said method is conducted in vivo, ex vivo, in vitro, and/or ex vitro; and/or said biological object is transilluminated and/or epi-illuminated with electromagnetic radiation prior to and/or during said detecting step.

In certain embodiments, any one or more of the following may hold: said detected electromagnetic radiation has a wavelength from about 200 nm to about 1200 nm; said detected electromagnetic radiation comprises infrared light, near-infrared light, visible light, and/or ultraviolet light; said physical (and/or supervenient) property variation comprises a variation of electromagnetic radiation absorption and/or scattering in at least a portion of said heterogeneous diffuse object; and/or said physical (and/or supervenient) property variation comprises macroscopic variation and/or microscopic variation.

In certain embodiments, said image is a planar (and/or two-dimensional) image. In certain embodiments, said image is used to generate a tomographic image. For example, said image may be one image among a number of pairs of two-dimensional emission/intrinsic images that are altered to correct for waveguiding (e.g., light tunneling), then are used thereafter for tomographic reconstruction. However, in alternative embodiments, a tomographic image itself, is altered to correct for waveguiding. In certain embodiments, the image is displayed, printed, stored, or otherwise fixed in tangible medium.

In certain embodiments, said detected electromagnetic radiation comprises light emitted by a probe or agent, wherein said probe or agent is within said heterogeneous diffuse object and/or on a surface of said heterogeneous diffuse object. In certain embodiments, said probe or agent comprises a fluorophore. In certain embodiments, the method includes the step of administering said probe or agent to said heterogeneous diffuse object. The probe may be, for example, a near-IR probe.

The description of elements of the embodiments of other aspects of the invention can be applied to this aspect of the invention as well.

In another aspect, the invention relates to a method for compensating an image for waveguiding effects, the method comprising: (a) detecting light emanating from at least part of a heterogeneous diffuse object at one or more wavelengths of excitation light, thereby acquiring an excitation (or intrinsic) image; (b) detecting light emanating from at least part of said heterogeneous diffuse object at one or more wavelengths of light emitted by a probe or agent, thereby acquiring a detected emission image, wherein said probe or agent emits said (emitted) light as a result of excitation by said excitation light and wherein said probe or agent is within said heterogeneous diffuse object and/or on a surface of said heterogeneous diffuse object; (c) creating an estimated emission image using at least said excitation (intrinsic) image; and (d) altering said detected emission image using at least said estimated emission image, thereby compensating said detected emission image for waveguiding effects (e.g., thereby reducing or eliminating effect(s) of optical property variation in said heterogeneous diffuse object). Here, "light" is not necessarily limited to visible light—"light" as used here can include infrared, near-infrared, visible, and ultraviolet electromagnetic radiation. In alternative embodiments, "light" may include electromagnetic radiation having wavelengths outside the visible and near-visible spectrum, for example, x-rays, gamma rays, radio frequency waves, and/or ultrasound waves. The steps (a)-(d) may be performed in any order. In certain embodiments, step (c) and/or step (d) is/are iterative.

In certain embodiments, step (a) and/or step (b) comprises detecting light transmitted through at least part of said heterogeneous diffuse object. In certain embodiments, any one or more of the following may hold: said heterogeneous diffuse object comprises a biological object; said biological object is a member selected from the group consisting of an animal, a mammal, a human, and a plant; said biological object comprises a biological tissue; said method is conducted in vivo, ex vivo, in vitro, and/or ex vitro; said biological object is transilluminated and/or epi-illuminated with said excitation light; said excitation light (detected in step (a)) has a wavelength from about 200 nm to about 1200 nm; said excitation light (detected in step (a)) comprises infrared light, near-infrared light, visible light, and/or ultraviolet light; said light emitted by said probe or agent (emission light detected in step (b)) has a wavelength from about 200 nm to about 1200 nm; said light emitted by said probe or agent (emission light detected in step (b)) comprises infrared light, near-infrared light, visible light, and/or ultraviolet light; and/or said light emitted by said probe or agent comprises fluorescent light (e.g., said probe or agent comprises a fluorophore). The probe may be, for example, a near-IR probe.

In certain embodiments, the method further includes the step of administering a/said probe or agent to said heterogeneous diffuse object (e.g., by injection, i.v., subcutaneous, oral administration, etc.). In certain embodiments, step (c) comprises applying a statistical estimator to said excitation (intrinsic) image to create said estimated emission image. In certain embodiments, said statistical estimator comprises a Kalman filter a Wiener filter, a maximum likelihood estimator, an independent component analysis technique, and/or any statistical estimator applied to a linear model. Independent component analysis refers to a computational method to separate a multivariate signal into its additive subcomponents, assume mutual statistical independence among the latter. Maximum likelihood estimation is a statistical method to calculate an optimal way of fitting a mathematical model to a set of data using various optimization algorithms, such as mean-squared error, etc.

In certain embodiments, any one or more of the following may hold: step (d) comprises subtracting said estimated emission image from said detected emission image; the method may include determining a coincidence mask from said excitation (intrinsic) image and said detected emission image; step (d) comprises subtracting said estimated emission image from said detected emission image to obtain a residual image, and applying said coincidence mask to said residual image to obtain said waveguiding-compensated emission image; and/or said coincidence mask identifies small and intense pixel subsets common to both said detected emission image and said excitation (intrinsic) image.

In certain embodiments, said excitation (intrinsic) image is a planar (and/or two-dimensional) image; and/or said detected emission image is a planar (and/or two-dimensional) image. In certain embodiments, said two-dimensional excitation (intrinsic) image and/or said two-dimensional emission image is/are used to generate a tomographic image. For example, the method may include obtaining a number of pairs of two-dimensional emission/intrinsic images that are altered to correct for waveguiding (e.g., light tunneling), then are used thereafter for tomographic reconstruction. However, in alternative embodiments, a tomographic image itself, is altered to correct for waveguiding. In certain embodiments, the image is displayed, printed, stored, or otherwise fixed in tangible medium.

In certain embodiments, the method further includes repeating steps (a)-(d) [in any order] to obtain a plurality of emission images compensated for waveguiding effects. For example, any of the following may hold: said plurality of waveguiding-compensated emission images are two-dimensional images; said plurality of waveguiding-compensated emission images comprises or is used to obtain one or more tomographic images; and/or said plurality of waveguiding-compensated emission images is used to obtain one or more tomographic images (e.g., used for tomographic reconstruction). In certain embodiments, the method includes determining a Born ratio from one or more of said waveguiding-compensated emission images and further masking said one or more waveguiding-compensated emission images (e.g., prior to tomographic reconstruction). For example, the Born ratio is computed from said one or more waveguiding-compensated emission images and/or said excitation (intrinsic) images; e.g., the intrinsic image(s) may be used to compute the denominator of the Born ratio.

In certain embodiments, the method obtains one or more tomographic images which include a concentration map of the agent or probe in the heterogeneous diffuse object. In certain embodiments, the concentrations for the concentration map are determined using calibration measurements of a phantom (physical mock-up) of the heterogeneous diffuse object.

The description of elements of the embodiments of other aspects of the invention may be applied to this aspect of the invention as well.

In yet another aspect, the invention relates to a method for compensating an image for waveguiding effects, the method comprising: (a) detecting light emanating from at least part of a heterogeneous diffuse object at one or more wavelengths of excitation light, thereby acquiring an excitation (or intrinsic) image; (b) detecting light emanating from at least part of said heterogeneous diffuse object at one or more wavelengths of light emitted by a probe or agent, thereby acquiring a detected emission image, wherein said probe or agent emits said (emitted) light as a result of excitation by said excitation light and wherein said probe or agent is within said heterogeneous diffuse object and/or on a surface of said heterogeneous diffuse object; (c) determining a coincidence mask from said excitation (intrinsic) image and said detected emission image; and (d) altering said detected emission image using at least said coincidence mask, thereby compensating said detected emission image for waveguiding effects (e.g., thereby reducing or eliminating effect(s) of optical property variation in said heterogeneous diffuse object). The steps may be performed in any order. In certain embodiments, step (a) and/or step (b) comprises detecting light transmitted through at least part of said heterogeneous diffuse object. In certain embodiments, said coincidence mask identifies small and intense pixel subsets common to both said detected emission image and said excitation (intrinsic) image.

In certain embodiments, one or more of the following hold: said heterogeneous diffuse object comprises a biological object; said biological object is a member selected from the group consisting of an animal, a mammal, a human, and a plant; said biological object comprises a biological tissue; said method is conducted in vivo, ex vivo, in vitro, and/or ex vitro; said biological object is transilluminated and/or epi-illuminated with said excitation light; said excitation light (detected in step (a)) has a wavelength from about 200 nm to about 1200 nm; said excitation light (detected in step (a)) comprises infrared light, near-infrared light, visible light, and/or ultraviolet light; said light emitted by said probe or agent (emission light detected in step (b)) has a wavelength from about 200 nm to about 1200 nm; said light emitted by said probe or agent (emission light detected in step (b)) comprises infrared light, near-infrared light, visible light, and/or ultraviolet light; and/or said light emitted by said probe or agent comprises fluorescent light (e.g., said probe or agent comprises a fluorophore). The probe may be, for example, a near-IR probe.

In certain embodiments, the method includes the step of administering a/said probe or agent to said heterogeneous diffuse object (e.g., by injection, i.v., subcutaneous, oral administration, etc.).

In certain embodiments, the method further includes repeating steps (a)-(d) [in any order] to obtain a plurality of emission images compensated for waveguiding effects. For example, any of the following may hold: said plurality of waveguiding-compensated emission images are two-dimensional images; said plurality of waveguiding-compensated emission images comprises or is used to obtain one or more tomographic images; and/or said plurality of waveguiding-compensated emission images is used to obtain one or more tomographic images (e.g., used for tomographic reconstruction). In certain embodiments, the method includes determining a Born ratio from one or more of said waveguiding-compensated emission images and further masking said one or more waveguiding-compensated emission images (e.g., prior to tomographic reconstruction). For example, the Born ratio is computed from said one or more waveguiding-compensated emission images and/or said excitation (intrinsic) images; e.g., the intrinsic image(s) may be used to compute the denominator of the Born ratio.

The description of elements of the embodiments of other aspects of the invention may be applied to this aspect of the invention as well.

In still another aspect, the invention relates to a method of imaging a region within an object, the method comprising: (a) administering to said object a probe comprising a fluorophore (e.g., near-infrared fluorophore); (b) directing excitation light (e.g., near-infrared excitation light) into (and/or onto) said object at multiple locations; (c) detecting excitation light emanating from said object, thereby acquiring an excitation (intrinsic) image; (d) detecting fluorescent light emitted from said probe within (or on a surface of) said object, thereby acquiring a detected emission image; and (e) processing data from said excitation (intrinsic) image and said detected emission image to provide a representation of said region within said object, said representation compensated for waveguiding effects, wherein step (e) comprises (one or both of): (i) creating an estimated emission image using at least said excitation (intrinsic) image and altering said detected emission image using at least said estimated emission image; and/or (ii) determining a coincidence mask from said excitation (intrinsic) image and said detected emission image; and altering said detected emission image using at least said coincidence mask.

In certain embodiments, any one or more of the following holds: step (c) comprises detecting excitation light transmitted through at least part of said object; said excitation light emanating from the object is detected at multiple locations;

said fluorescent light is (or comprises) near-infrared light; said representation of said region is a tomographic representation; step (e) comprises simulating photon propagation at said excitation wavelength and simulating photon propagation at said emission wavelength to obtain a prediction of one or more quantitative measurements of said probe; step (e) comprises determining a concentration of said probe; and/or step (e) comprises determining a quantity of said probe accumulated in said region within said object. The probe may be, for example, a near-IR probe.

In certain embodiments, the method further comprises combining said waveguiding-compensated emission image with magnetic resonance, x-ray computed tomography, ultrasound, single photon emission tomography, and/or positron emission tomography imaging data.

In certain embodiments, step (e) of the method includes determining a concentration (or a concentration map) of the probe in the object using calibration measurements of a phantom (physical mock-up) of the object.

The description of elements of the embodiments of other aspects of the invention may be applied to this aspect of the invention as well.

In still another aspect, the invention relates to a fluorescence molecular tomography imaging system comprising: an excitation light source; an optical imaging chamber configured to direct excitation light from said excitation light source into an object disposed within said chamber at multiple locations; a detector configured to detect at multiple locations excitation light emanating from said object (thereby acquiring an excitation (intrinsic) image) and fluorescent light emitted from one or more probes within (or on a surface of) said object (thereby acquiring a detected emission image); and a processor configured to process data from said excitation (intrinsic) image and said detected emission image to provide a representation of said region within said object, said representation compensated for waveguiding effects, wherein said processor is configured to perform one or both of the following: (i) create an estimated emission image using at least said excitation (intrinsic) image and alter said detected emission image using at least said estimated emission image; and/or (ii) determine a coincidence mask from said excitation (intrinsic) image and said detected emission image and alter said detected emission image using at least said coincidence mask.

The description of elements of the embodiments of other aspects of the invention may be applied to this aspect of the invention as well.

BRIEF DESCRIPTION OF DRAWINGS

The objects and features of the invention can be better understood with reference to the drawings described below, and the claims. In the drawings, like numerals are used to indicate like parts throughout the various views.

DETAILED DESCRIPTION

Figure 1:
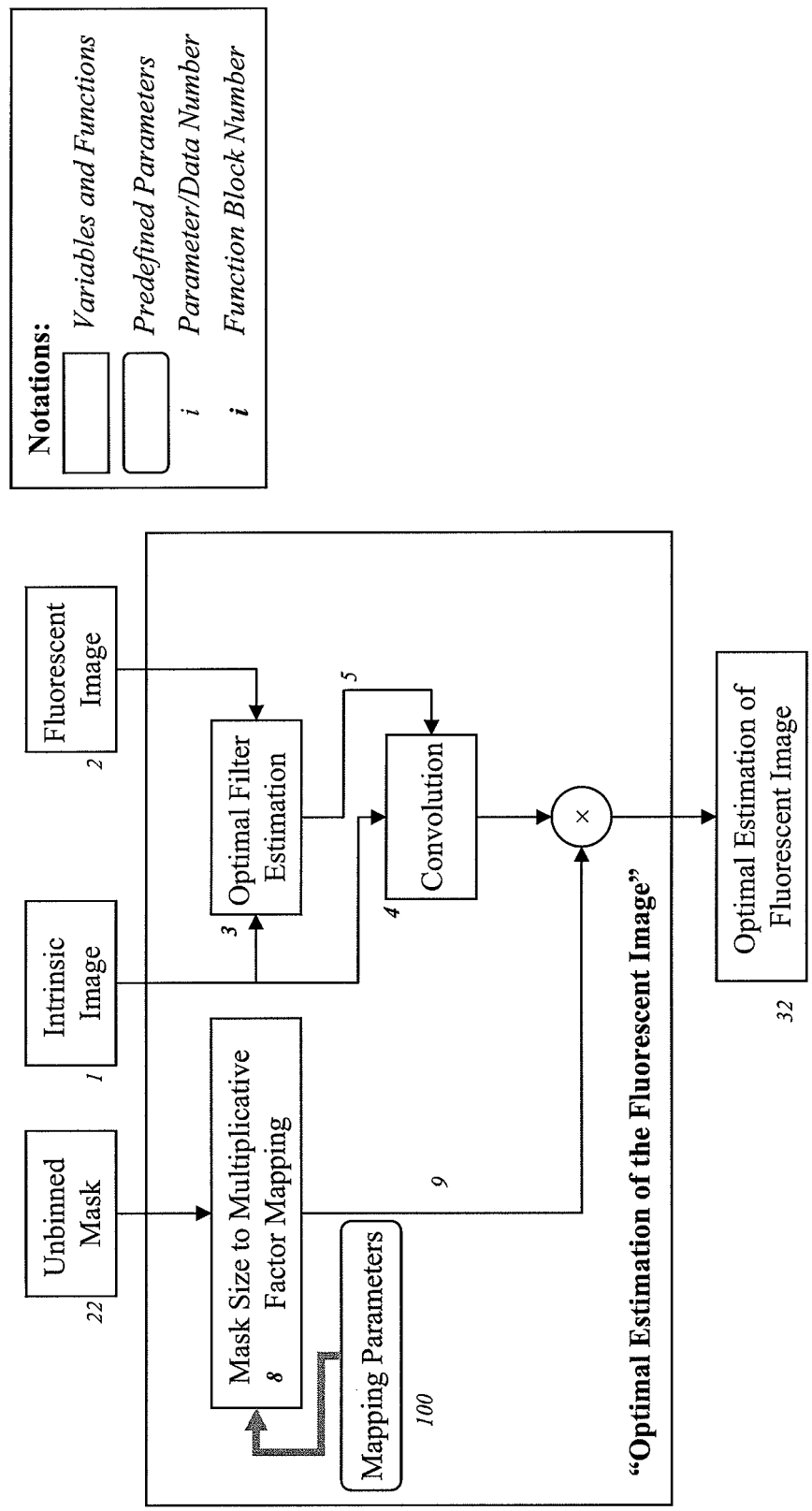
FIG. 1 is a block diagram of an optimal estimator of a fluorescent image from an intrinsic image, according to an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

This application incorporates-by-reference U.S. Patent Application Publication No. US2004/0015062 and International (PCT) Patent Application Publication No. WO2007/111669.

Headers are used herein to aid the reader and are not meant to limit the interpretation of the subject matter described.

As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout).

In addition to fluorescence molecular tomographic images, the term "tomographic image" may include, for example, any optical tomographic image, an x-ray tomographic image, as well as a tomographic image generated by magnetic resonance, positron emission tomography (PET), magnetic resonance (MR), single photon emission computed tomography (SPECT), ultrasound, and/or any combination of such images.

As used herein, the term "excitation image" is understood to mean an image acquired at one or more wavelengths corresponding to that of an exposing light source.

The term "intrinsic image" is understood to mean an image acquired at one or more wavelengths corresponding to that of an exposing light source, said exposing light emanating from the object being imaged.

The terms "emission image" are understood to mean an image acquired at one or more wavelengths corresponding to the emission wavelength(s) of an agent or probe. For example, a "fluorescence image" is an emission image of a fluorescent agent or probe.

The term "residual image" is understood to mean an image resulting from application (e.g., subtraction) of a corrective term, for example an image, from an original image, for example an emission image.

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume, and the three-dimensional map may be displayed in two-dimensions.

As used herein, the term "electromagnetic radiation" is understood to mean, for example, self-propagating waves in space of electric and magnetic components that oscillate at right angles to each other and to the direction of propagation, and are in phase with each other. Electromagnetic radiation includes, for example, radio waves, microwaves, read and infrared light, visible light, ultraviolet light, X-rays and gamma rays.

As used herein, the terms "estimator", "signal estimation" or "statistical estimator" or "filter" are understood to mean a method, system, subsystem, routine, or subroutine for obtaining a numerical estimate of an unknown quantity of interest based at least in part on observable data As used herein, the term "optimal estimator" is understood to mean a method, system, subsystem, routine, or subroutine for obtaining a numerical estimate of an unknown quantity of interest based at least in part on observable data by minimizing or maximizing the value of a given criterion function.

As used herein the term "coincidence mask" or "coincidence masking" refers to, for example, the application of a defined area or region of interest within an image for the purpose of detecting the presence or absence of a similar event in the corresponding area or region of interest in another image.

As used herein the term "image acquisition device" includes any detector of electromagnetic radiation including, but not limited to, CCD camera, photomultiplier tubes, photodiodes, and avalance photodiodes.

As used herein the term "waveguided" refers to the preferential guiding of electromagnetic radiation within a medium along paths of lower resistance.

The methods of waveguide compensation proposed here use methods of signal estimation and/or coincidence masking as described further below to compensate for waveguided electromagnetic radiation from heterogeneous diffuse objects prior to tomographic and/or planar image construction and/or analysis. An illustrative, non-limiting description is provided for a method of waveguide compensation for light used to topographically image heterogeneous diffuse objects.

In this case, waveguided light may result from the use of fluorescent agents, fluorescent proteins, and/or endogenously expressed fluorescent reporters (i.e., expressed fluorescent molecules) and/or molecules (i.e., endogenous biological molecules that exhibit auto-fluorescence). The steps of the method are described in reference to the flowcharts presented in FIG. 1-4.

Figure 5:
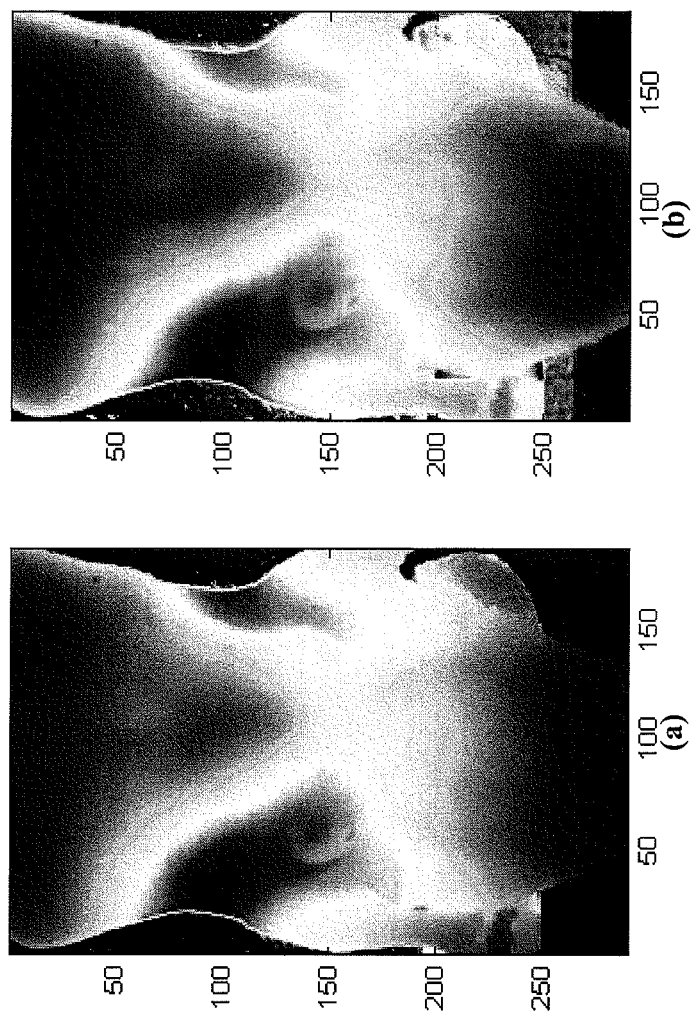
FIG. 5 presents an exemplary dataset of a mouse bearing HT-29 human colorectal cancer tumor xenografts injected with an activatible fluorescent molecular probe (a) intrinsic image at the excitation wavelength (b) fluorescent image at the emission wavelength. The images are scaled by the logarithm of pixel intensity.

The intrinsic and fluorescent images acquired in a typical tomographic scan are highly correlated in a spatial sense. FIGS. 5(*a*) and (*b*) show illustrative in vivo images obtained at the excitation and emission wavelengths respectively for a given source position. In this specific case, the components of the fluorescent image which are not correlated well with the intrinsic image are mostly due to emission of fluorescence present in the targeted regions. In this specific case, fluorescence is being produced predominantly by an exogenously administered fluorescent contrast agent/probe. The components in the fluorescent image which are highly correlated with the intrinsic image are mostly contributed by the emission of background fluorescence (i.e., mostly due to endogenous fluorescence, also known as autofluorescence) as well as the waveguided emission from the fluorescent probe, both of which are highly undesirable.

Based on this observation, the uncorrelated components of the fluorescent image are separated from the correlated components through signal estimation of the fluorescent images from the intrinsic images. The parts of the fluorescent images that cannot be estimated, or predicted, from the intrinsic images are referred to as the "residual images" (also referred to here as "adjusted fluorescent images"). Residual images thus primarily consist of the desirable fluorescence signal emanating from the target areas.

As a non-limiting example, let $F_1, \ldots, F_N$ denote the images obtained by the image acquisition device at the emission wavelength, i.e. the fluorescent images, for the N source positions. Similarly, denote images obtained at the excitation wavelength (i.e. the intrinsic images) by $I_1, \ldots, I_N$. Each of these images is a matrix of size $P_x \times P_y$, where x and y are the number of detector elements in each direction. In a preferred embodiment of the method, we assume the dark noise of the acquisition device detectors to be already subtracted from these images. The estimation or prediction of the fluorescent images from the intrinsic images can be performed in the most general form as:

$$R_i = F_i - \mathcal{P}_i(F_1, \ldots, F_N, I_1, \ldots, I_N), i=1, \ldots, N \qquad (1)$$

where $R_i$ represents the $i^{th}$ residual image. The function $P_i$ represents the estimator function. In this general form, all the fluorescent images and intrinsic images from all sources are used in estimating the fluorescent image, $F_i$.

Various statistical estimators or filtering methods, such as Kalman or Wiener filtering, can be used to obtain estimations of the fluorescent image from one or more intrinsic images. For a general review of statistical estimator or filtering methods see, for example, *Statistical Digital Signal Processing and Modeling* by M. H. Hayes (John Wiley and Sons, 1996). In the following example, we present a non-limiting example based on a Wiener statistical estimator for this purpose. In the specific implementation of Eq. 1 as described herein as an illustrative embodiment of the method, each fluorescent image $F_i$ is estimated from only its corresponding intrinsic image, $I_i$ using a linear filter. In other words, we have:

$$R_i = F_i - \beta \times G_i * I_i, i=1, \ldots, N \qquad (2)$$

where $G_i$ is a 2D digital linear filter and * denotes the convolution operator. Equation 2 codifies the linear estimation of $F_i$ from $I_i$. It should be noted that in a preferred embodiment of the method, the residual image can be clipped at 0 (i.e., all the negative numbers in $R_i$ are set to 0 after the subtraction in Eq. 2). The parameter β is a constant non-negative real number smaller than 1 and is determined independently of it, as described below. An illustrative implementation of this step is presented in FIG. 1, where block 21 encapsulates the processing of one frame of the intrinsic image $I_i$ 1 and fluorescent image $F_i$ 2 for the $i^{th}$ source position. The filter or statistical estimator $G_i$ is the variable 5 and the application of the filter to the intrinsic image scaled by the parameter □ is the variable 32. The calculation of parameter β 9 involves blocks 22, 8 and 100, as detailed below. The convolution operator in Eq. 1 is shown in block number 4. The subtraction in Eq. 2 is block 26 in FIG. 4.

Figure 2:
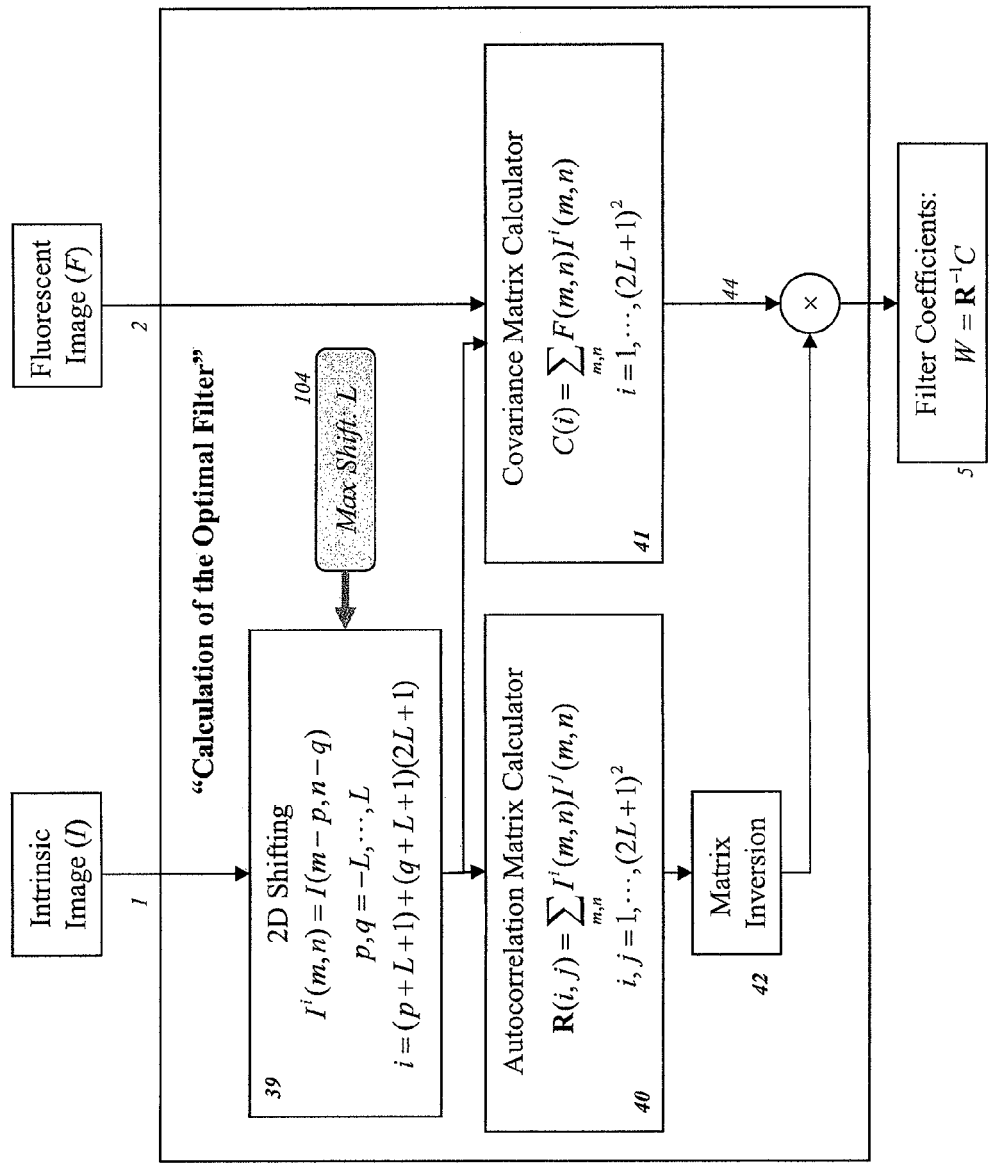
FIG. 2 is a block diagram depicting the processing steps for the optimal estimation filter, according to an illustrative embodiment of the invention.
Figure 3:
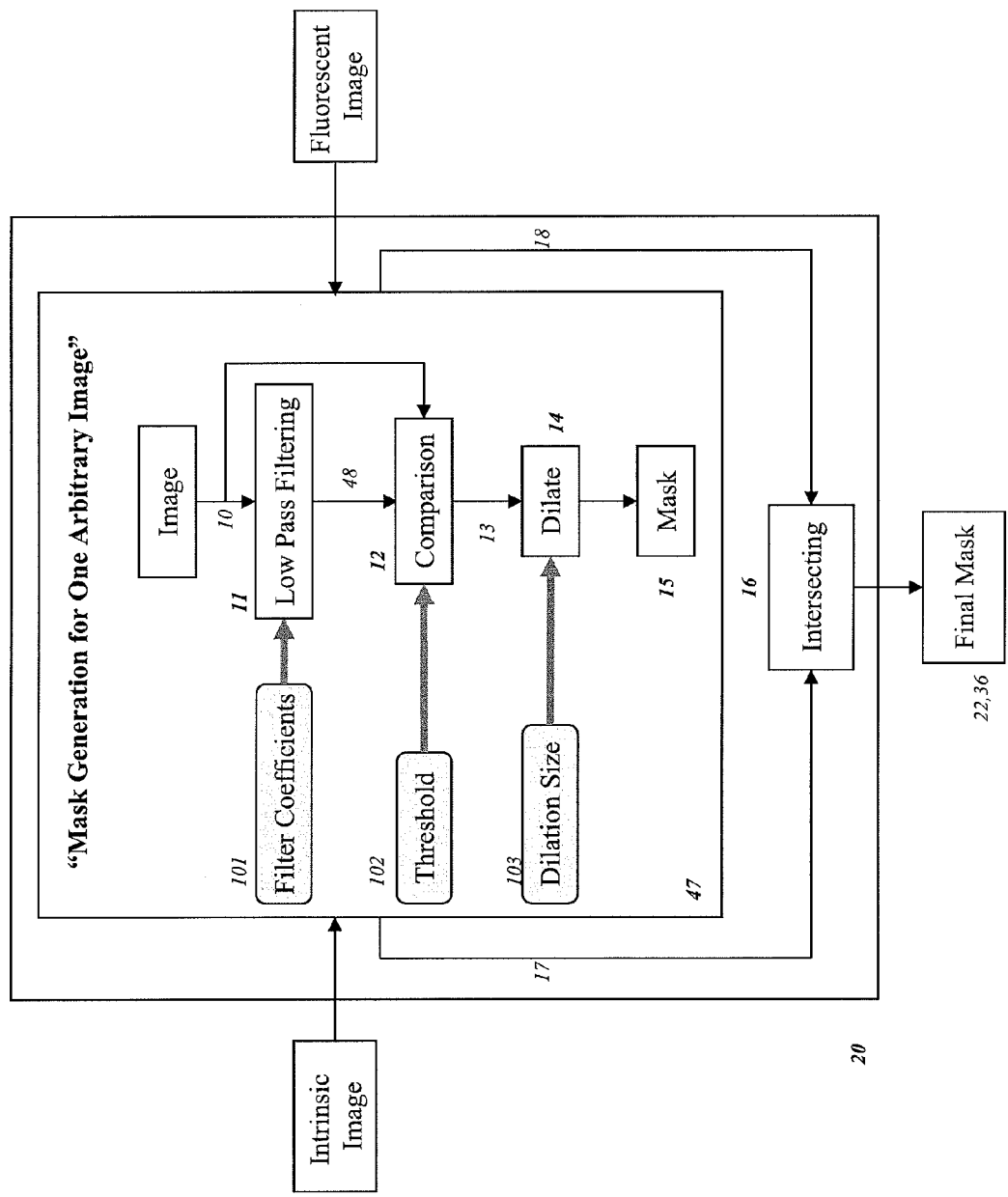
FIG. 3 is a block diagram of a coincidence mask generator, according to an illustrative embodiment of the invention.
Figure 4:
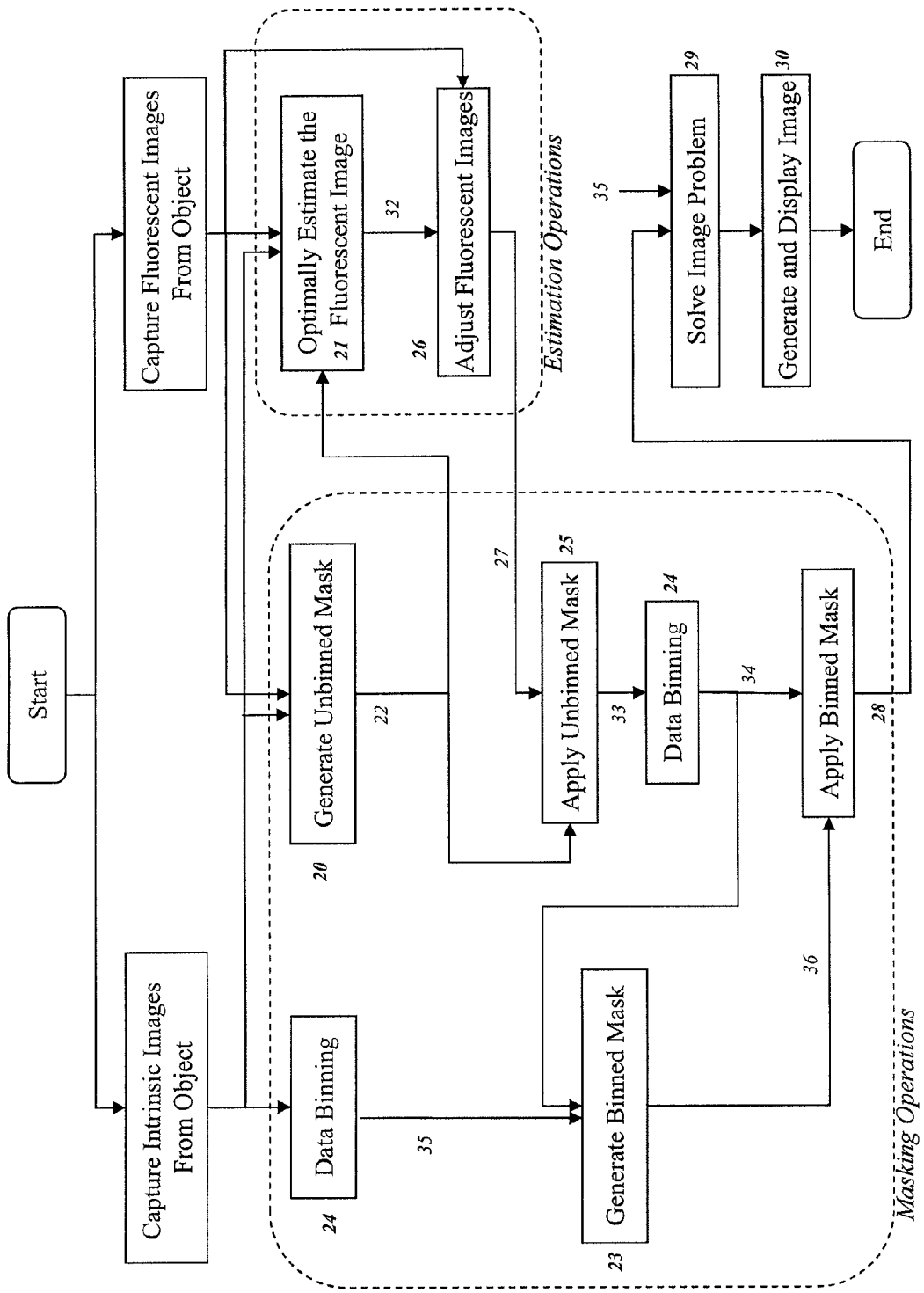
FIG. 4 is a block diagram of an exemplary embodiment of a complete waveguiding compensation method, according to an illustrative embodiment of the invention.

As detailed in FIG. 2, the filter or statistical estimator $G_i$ is derived from the intrinsic and fluorescent images. We assume this filter is of size of (2L+1) pixels×(2L+1) pixels, where L represent the maximum shift of the filter in the x or y directions. The larger the parameter L, the higher the number of degrees of freedom in the signal estimation, and therefore the better the signal estimation. However, increasing L can significantly increase the complexity of calculating $G_i$. For a given value of L, the filter $G_i$ for a set of images $I_i$ and $F_i$ is determined in reference to block number 3 in FIG. 1 and further expanded in FIG. 2. Referring now to FIG. 2, parameter L is shown as block 104. The criterion for signal estimation is the energy of the residual signal:

$$G_i = \underset{g}{\mathrm{argmin}} \|F_i - g * I_i\|_2 \qquad (3)$$

The solution to this equation can be obtained by differentiation with respect to elements of g. Setting the derivative equal to zero, results in the following equation:

$$RV(G_i) = C \qquad (4)$$

where R and C denote, respectively, the autocorrelation matrix of $I_i$ and the covariance vector between $F_i$ and $I_i$. The operator V converts a matrix to a column vector. For instance:

$$V\left(\begin{bmatrix} 1 & 0 & 5 \\ 4 & -1 & 7 \end{bmatrix}\right) = [1, 4, 0, -1, 5, 7]^T \qquad (5)$$

It is important to note that this approach adapts the Wiener-Hopf signal estimation of a stationary stochastic process to a deterministic image estimation problem. See for example (Hayes, 1996, Chapter 7) for a derivation of the Wiener-Hopf equations. The autocorrelation matrix R has a size of $(2L+1)^2 \times (2L+1)^2$ and is defined as:

$$R(k, j) = \sum_{m,n} I_i^k(m, n) I_i^j(m, n) \qquad (6)$$

where $I_i^k$ is the a shifted version of $I_i$ and defined as:

$$I_i^k(m, n) = I_i(m - p, n - q) \qquad (7)$$
$$p, q = -L, \ldots, L$$
$$k = (p + L + 1) + (q + L + 1)(2L + 1)$$

The steps for finding R are summarized in block 40. The shifting operations of Eq. 7 are shown in block 39. The covariance vector C is defined as:

$$C(k) = \sum_{m,n} F_i(m, n) I_i^k(m, n) \qquad (8)$$

and is shown as block 41, with the output covariance vector as line 44. The optimal statistical estimator $G_i$ is found by solving Eq. 4, which involves inverting the autocorrelation matrix R, a step shown as block 42. The solution is given in block 5, where $W = V(G_i)$.

Figure 6:
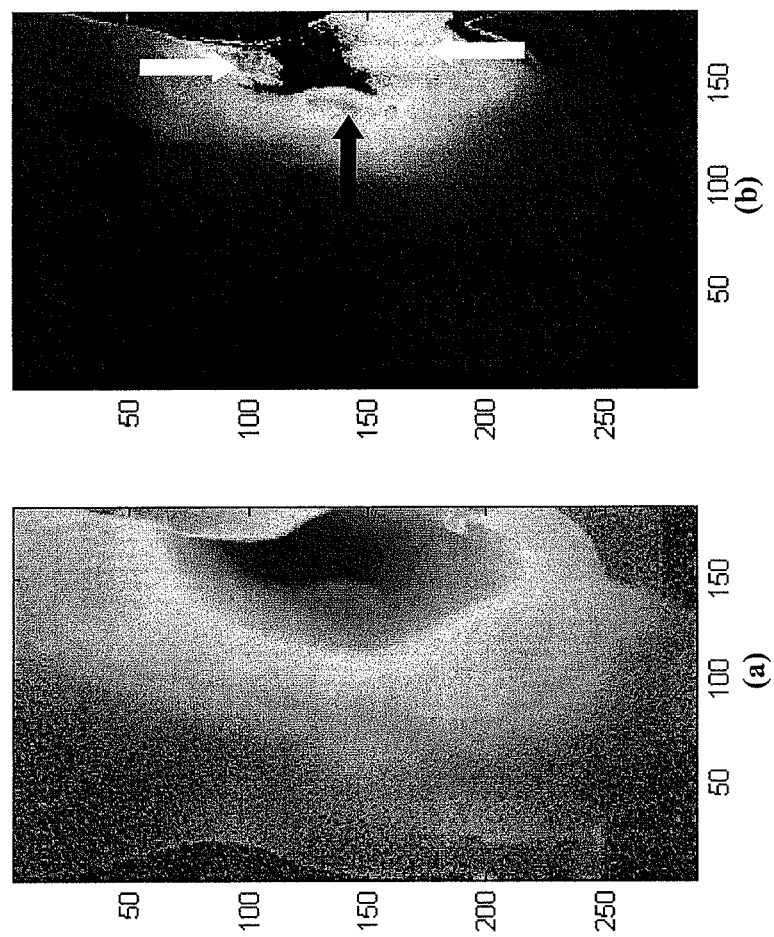
FIG. 6 presents an exemplary dataset of the same subject illustrating intermediate processing steps of the present invention (a) fluorescent image (log scale) (b) residual image (linear scale).

To illustrate the steps detailed above with an example, the estimation methodology is applied to an in vivo animal image pair shown in FIG. 5 with L=2. The resulting pair of residual image and original fluorescent image is depicted in FIG. 6. FIG. 6(a) shows the original fluorescent image (logarithmic scale, to enhance the dynamic range limitations in the signal) and FIG. 6(b) shows the residual image (linear scale). As can be observed from FIG. 6(b), the desirable fluorescent signal from the tumor implanted in the animal (horizontal black arrow) is more readily discernable and better differentiated from background in the residual image than the original fluorescent image.

While the spurious components of fluorescence due to the waveguiding are largely removed from the residual images, as illustrated in FIG. 6(b), some undesirable fluorescence still remains (vertical white arrows in FIG. 6(b)). This is due to the limited size of the filter or statistical estimator used in the linear estimator. To remove these and achieve a more effective and robust elimination of the spurious components in the fluorescent images, a "coincidence mask" can optionally be created and applied to the residual image. This mask is created on the grounds that the waveguided areas in both fluorescent and intrinsic images follow similar patterns. In particular, they contribute areas of significant intensity and relatively small size in the images. Using this observation, a spatial coincidence mask indicating a map of the waveguided areas in the fluorescent image can be obtained as described below.

The map of the areas where waveguiding could have occurred is referred to as a mask. Once a mask is identified in each image, another map of waveguiding is generated as the intersection of the two masks obtained from the fluorescent and intrinsic images. This map is referred to as the coincidence mask and denotes areas where waveguiding has most likely happened, as it has happened in both intrinsic and fluorescent images. In other words, the coincidence mask identifies the pixel subsets that are bright and relatively small in both the intrinsic and fluorescent image pairs. The steps involved in the generation of the coincidence mask are described in reference to FIG. 3.

If X and Y denote an intrinsic image and its corresponding fluorescence image respectively, the method is applicable regardless of whether or not any binning has been applied to any images. The method of obtaining the mask for either image is identical, and so the steps of mask generation for intrinsic image X are described here and are encompassed in block 47. The image for which a mask is obtained (here X) is denoted by line 10.

The mask derived from image X represents a map of the areas where waveguiding is considered to represent a primary contribution to the image. Accordingly, the small and bright spots in X can be identified. From this, the pixels that are greater than a fraction of some statistic of the neighboring pixels can be selected. As an example, one can define $I_X$ as:

$$I_X\{(i,j)|X(i,j)>\alpha \times K(i,j)\}, \text{ where } K=F^*X \quad (9)$$

where F is a low-pass filter, shown by block 101. $I_X$ then represents the set of all pixels that are larger than a fraction, denoted by the real number $\square>1$, of the weighted mean of the neighboring pixels, where such weighting is specified by F. The larger the span of the filter F, the larger the spots we are allowing into the map. The larger the parameter a, the more restrictive the mask becomes in terms of the brightness of the areas we are allowing into the map. The filtering operation is illustrated as block 11, and matrix K is line 48. The threshold parameter $\square$ is block 102. The comparison criterion in Eq. 9 is shown as block 12. The set $I_X$ is line 13.

The mask for image X, $I_X$, is given in terms of $I_X$, as:

$$I_X = \left\{ \bigcup_{\mu,\gamma} I_X(\mu, \gamma) \right\} \quad (10)$$

where $I_X(\mu,\gamma)$ is the mask $I_X$ shifted in x and y directions by $\square$ and $\gamma$ pixels. This operation essentially dilates the mask to cover up any small secluded holes. The dilation operation is given in block 14 and the set $I_X$ is block 17 and $I_Y$ is block 18. The parameters $\gamma$ and $\mu$ are shown as block 103. The mask for the fluorescent image Y, $I_Y$, is found in identical fashion. The resulting coincidence mask, I, is then given by:

$$I=I_X \cap I_Y \quad (11)$$

Figure 7:
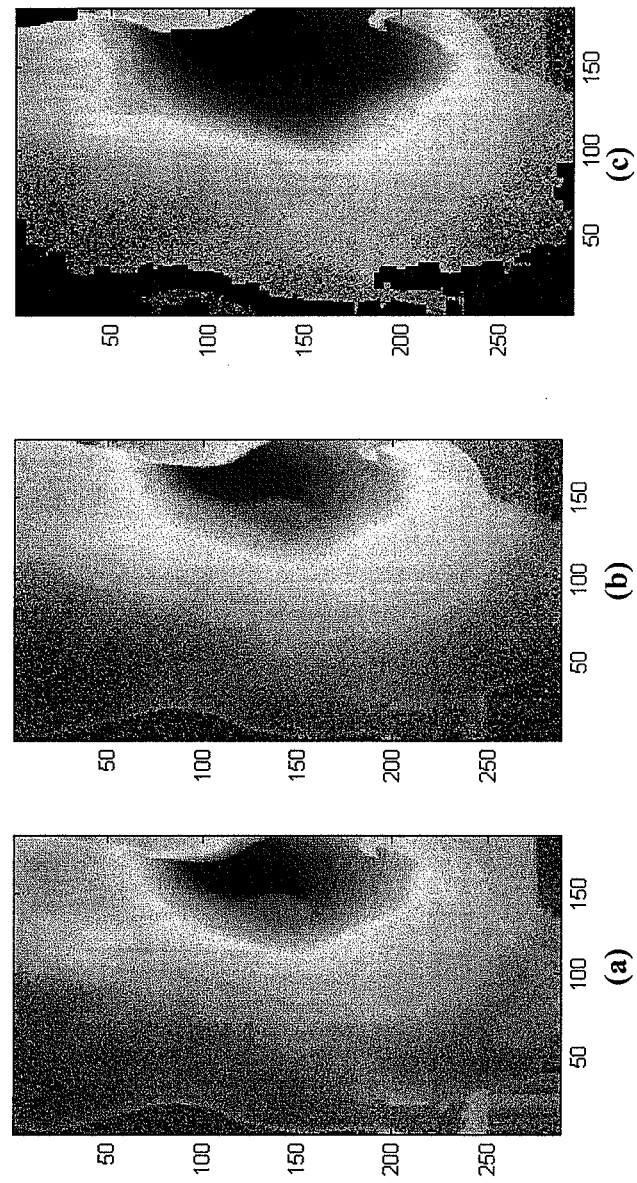
FIG. 7 presents an exemplary dataset of the same subject illustrating intermediate processing steps of the present invention (a) intrinsic image (log scale) (b) fluorescent image (log scale) (c) The result of applying the coincidence mask to the fluorescent image (log scale).

The intersection operation is block 16 and the coincidence mask is block 22,36. The coincidence mask I then represents a map of the areas where waveguiding mainly contributes to the fluorescent image. FIG. 7c shows the result of applying the coincidence mask to the intrinsic and fluorescent images shown in FIGS. 7(a) and (b), respectively. The images are all shown on a logarithmic scale. As seen, the coincidence mask primarily covers the areas of waveguided light in the original images.

Figure 9:
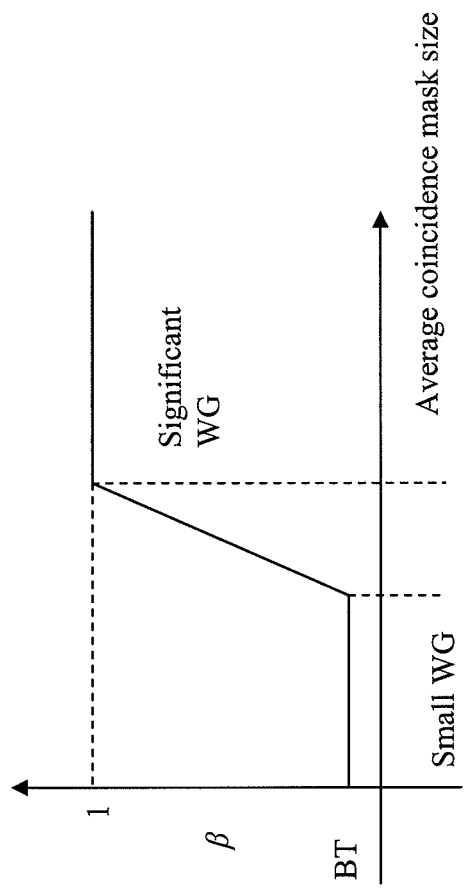
FIG. 9 illustrates the mapping of the average coincidence mask size to the parameter $\beta$, according to an illustrative embodiment of the invention.
Figure 10:
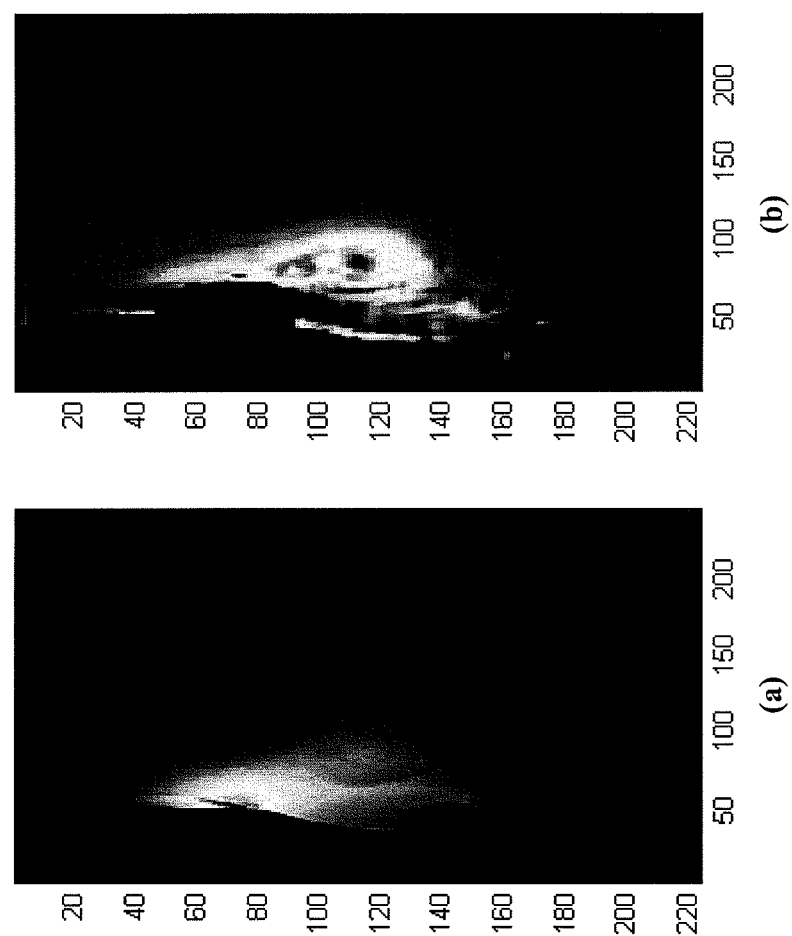
FIG. 10 presents another exemplary dataset of a mouse bearing HT-29 human colorectal cancer tumor xenografts injected with a physiological fluorescent molecular probe (a) fluorescent image (b) residual image masked by the coincidence mask, both images on a linear scale.

The coincidence mask I is derived for each pair $F_i$, $I_i$ of images where the index i represents the $i^{th}$ source position. The coincidence mask is used in two ways. First, it is used to derive the parameter $\beta$ used in Eq. 2 for scaling the estimated image that is subtracted from each fluorescent image. The parameter $\beta$ is set to its maximum, i.e. 1, if a high level of waveguiding is suspected. The average size of the coincidence masks obtained for all source positions can be used as a measure for determining the overall amount of waveguiding. FIG. 9 shows an illustrative mapping of the average coincidence mask size to the parameter $\beta$. In the case of no or very small waveguiding (typical of imaging phantoms and certain imaging of heterogeneous diffusive media/objects), the parameter $\beta$ is set to roughly a floor value referred to as the bleedthrough coefficient (BTC). The mapping of the average mask size to the parameter $\beta$ is block 8 and its parameters are block 100 in FIG. 1.

Figure 8:
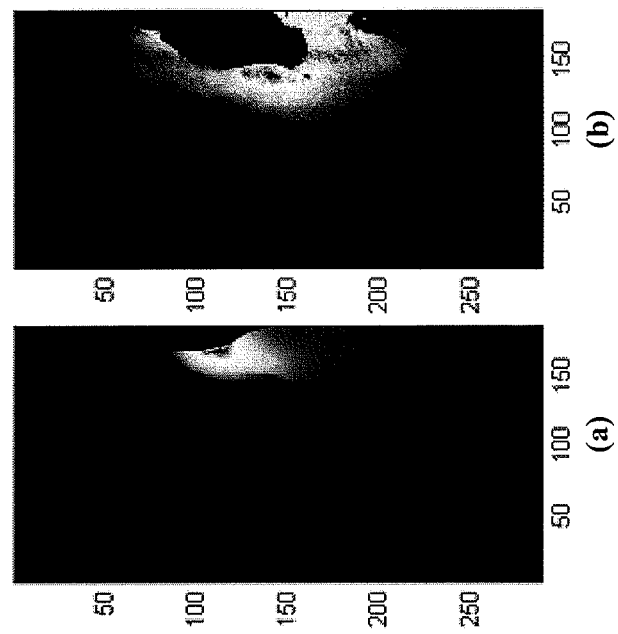
FIG. 8 presents an exemplary dataset of the same subject illustrating the inputs to and outputs from the present invention (a) fluorescent image (b) residual image masked by the coincidence mask, both images shown on a linear scale.

Secondly, the coincidence mask I generated in block 20 (FIGS. 3 and 4), is applied to the residual image $R_i$, line 27, to further mask out the areas of waveguided light that are left after the subtraction of the fluorescence estimate. This is done by setting the pixels identified by the coincidence mask in the residual image to zero (masking operation is block 25). The resultant image is line 33. The result of the subtraction of the estimate (shown in block 26), described by Eq. 2, following by masking of the residual image is shown in FIG. 8. FIG. 8(a) shows the original fluorescent image and FIG. 8(b) shows the adjusted fluorescent image masked by the coincidence mask. This masked residual image is considered the new fluorescent image. This fluorescent masked residual image can then be binned (block 24) for each virtual detector. The binned fluorescent and intrinsic images (lines 34 and 35, respectively) are further used to draw another coincidence mask (line 36), at the binned level. This mask is applied to the binned fluorescent image (result is line 28). This operation is done to further remove spurious components that might have arisen as the result of the binning and overall results in a more robust reduction of the waveguided light. This masked binned image, line 28, is finally provided, along with the binned intrinsic image (line 35) and can be provided to any reconstruction algorithm (block 29).

To further illustrate the invention, below is a non-limiting example of the waveguide compensation methods disclosed herein applied to Fluorescence Molecular Tomography.

Fluorescence Molecular Tomography (sometimes also referred to as Fluorescence Mediated (Molecular) Tomography) provides a method of in vivo imaging including the steps of administering to a subject an optical imaging probe; directing excitation light into the subject at multiple locations; detecting excitation light emanating from the subject; detecting optical light emitted from one or more probes within the subject; and processing data corresponding to both the detected excitation light emanating from the subject and the detected fluorescent light emitted from the probe within the subject, to provide a tomographic representation of the region within the subject. The processing of data corresponding to both the detected excitation light and detected fluorescent light comprises simulating photon propagation at the excitation wavelength and simulating photon propagation at the emission wavelength to obtain a prediction of one or more quantitative measurements of the probe, such as concentration or total accumulation in a region within the object, and can also include the additional steps of applying the statistical optimal estimation and coincidence masking techniques described herein to predict and compensate for waveguiding effects. The steps can also be repeated at predetermined interval, thereby allowing for the evaluation of the subject over time. The subject may be a vertebrate animal, for example, a mammal, including a human. The subject may also be a non-vertebrate (for example, C. elegans, drosophila, or another model research organism, etc.) used in laboratory research.

The method and algorithm accept as input raw scan images generated by a fluorescence molecular tomography (FMT) system acquisition of any object. As described in U.S. Pat. No. 6,615,063 "Fluorescence-Mediated Molecular Tomography", the text of which is incorporated herein by reference in its entirety, FMT-generated raw scan images contain images at both the excitation wavelength of the light source, called "intrinsic images", and at the emission wavelength of the contrast agent, interchangeably called "emission images" or "fluorescence images", for a multiplicity of source and/or detector locations. A predictive map of fluorescent light tunneling in the object is generated based on an estimate of light tunneling in the intrinsic images, and the strong spatial cross-correlation that exists between the intrinsic and emission images in object regions with significant waveguiding. To achieve this, an optimal estimation, for example a mean-square error (MSE) estimation, of the emission image is made based on its corresponding intrinsic image from the same source/detector pair. The residual between this optimal estimate and the original emission image thus yields an image of corrected fluorescence. This correction is further masked by a coincidence mask identifying the intersection of small, high intensity regions across both excitation and emission pairs, attributed to the waveguiding effect. The resulting final emission images are then used to form a Born ratio, which can be further masked if desired, prior to proceeding with FMT reconstruction.

The detected light preferably includes excitation light from the light source that has been transmitted through the object and fluorescent light emitted from one or more fluorophore within the object. Data corresponding to the excitation light transmitted through the object, or intrinsic light, can be used to correct/calibrate captured fluorescent measurements, thereby providing more accurate tomographic images. The one or more fluorophore emits fluorescent light as a result of excitation by the excitation light. Background fluorescence may be accounted for by obtaining background measurements and processing data corresponding to the captured fluorescent light accordingly. For example, the method may include the step of detecting a background signal, where the processing step includes generating a corrected measurement of the detected fluorescent light and/or a corrected measurement of the detected excitation light using data corresponding to the detected background signal, and using the corrected measurement(s) in the optical tomographic reconstruction. In certain embodiments, the processing step includes generating a corrected measurement of the detected fluorescent light and a corrected measurement of the detected excitation light using data corresponding to the detected background light, generating a calibrated fluorescent measurement from the corrected fluorescent measurement and the corrected excitation light measurement, and using the calibrated fluorescent measurement in the optical tomographic reconstruction.

Data corresponding to the detected light may be used as input in the optical tomographic and/or planar reconstruction, for example, in an iterative process. In certain embodiments, the steps of the method are repeated to obtain a plurality of tomographic and/or planar images.

In addition to tomographic imaging, the present invention is also applicable to in vivo planar imaging including the steps of administering to a subject a contrast agent or probe; allowing time for the contrast agent to distribute in the subject; positioning the subject in the imaging system; collecting the planar radiation data sets sequentially or simultaneously; applying waveguiding compensation to the planar data sets; and displaying the datasets as two-dimensional (2D) images either alone or in combination with another image.

Aspects of the two section, "Data Processing—Contact and Non-contact Optical Tomographic Systems" and "Data Processing—Free Space Optical Tomographic Systems" in Appendix B, attached herewith, are applicable to optical tomography and may be applied in the embodiments described herein. Also, the text of the following documents is incorporated herein by reference and this subject matter may be applied in the embodiments described herein: U.S. Pat. No. 6,615,063, U.S. Patent Application Publication No. US200410015062; International (PCT) Patent Application Publication No. WO03/102558; and International (PCT) Patent Application Publication No. WO2004/072906.

Optical imaging devices and measurement techniques that may be used in the systems and methods described herein include, but are not limited to, fluorescence imaging, luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography.

Commercially available systems that may be used in the systems and methods described herein include but are limited to, eXplore Optix and SoftScan (ART—Advanced Research Technologies), NightOWL II LB (Berthold Technologies), NanoSPECT and HiSPECT (Bioscan), Maestro FLEX and Nuance FLEX (Cambridge Research and Instrumentation—CRi), LightSpeed, BrightSpeed and MR Signa Series (GE Healthcare), Kodak In-Vivo Imaging FX Systems and Kodak Image Station 4000 series (KODAK and Carestream), Aquacosmos (Hamamatsu), CTLM and LILA Imaging Systems (Imaging Diagnostic Systems—IMDS), Odyssey Infrared Imaging System (LI-COR), IMRIS Neuro System (IMRIS), SPY and SPY-TMR Systems, HELIOS, LUNA, and OPTTX Imaging Systems (Novadaq), DYNOT Imaging System (NIRx), and IVIS Systems, IVIS Spectrum and IVIS Lumina (Xenogen and Caliper Life Sciences).

Systems of the invention may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

In certain embodiments, the invention features an in vivo imaging method for selectively imaging a subject containing two or more imaging probes simultaneously, wherein two or more imaging probes are administered to a subject, either at the same time or sequentially. The imaging probes can be any combination of optical or other imaging agents. A single imaging agent may serve as both an optical and other imaging modality agent, e.g., dual imaging agent. The method therefore allows the recording of multiple biological processes, functions or targets. The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

The invention can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone, including metastases), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarthritis). The methods of the invention can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the invention can also be used in identification and evaluation of cell death, injury, apoptosis, necrosis, hypoxia and angiogenesis. The methods and compositions of the invention can also be used in for monitoring trafficking and localization of certain cell types, including T-cells, tumor cells, immune cells, stem cells, and other cell types. In particular, this method may be used to monitor cell based therapies.

In certain embodiments, the systems and methods described herein can be used to image endogenous fluorescence in a subject. For example, a gene encoding a fluorescent protein, such as green or red fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed.

Imaging Probes

The imaging system and method can be used with a number of different imaging probes, for example, (1) probes that become activated after target contact (e.g., binding or interaction) (Weissleder et al., *Nature Biotech.*, 17:375-378, 1999; Bremer et al., *Nature Med.*, 7:743-748, 2001); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech.* 15:1271-1275, 1997); (5) quantum dot or nanoparticle-based imaging probes, including multivalent imaging probes; (6) non-specific imaging probes e.g., indocyanine green, AngioSense (VisEn Medical); (7) labeled cells (e.g., such as cells labeled using exogenous fluorophores such as VivoTag 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this invention, the imaging probes can be administered systemically or locally by injecting an imaging probe or by topical or other local administration routes, such as "spraying".

In particular, molecular imaging probes are a preferred type of imaging probe. A molecular imaging probe is a probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, optical imaging probes have excitation and emission wavelengths in the red and near infrared spectrum in the range 550-1300 or 400-1300 nm or about 440 and about 1100 nm, between about 550 and about 800 nm, between about 600 and about 900 nm. Use of this portion of the electromagnetic spectrum maximizes tissue penetration and minimizes absorption by physiologically abundant absorbers such as hemoglobin (<650 nm) and water (>1200 nm). Optical imaging probes with excitation and emission wavelengths in other spectrums, such as the visible and ultraviolet light spectrum, can also be employed in the methods of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); also WO 97/40104, WO 99/51702, WO 01/21624, and EP 1 065 250 A1; and Tetrahedron Letters 41, 9185-88 (2000); all of the above incorporated by reference herein.

Exemplary fluorochromes for optical imaging probes include, for example, the following: Cy5.5, Cy5, Cy7.5 and Cy7 (GE Healthcare); AlexaFlour660, AlexaFlour680, AlexaFluor790, and AlexaFluor750 (Invitrogen); VivoTag680, VivoTag-S680, VivoTag-5750 (VisEN Medical); Dy677, Dy682, Dy752 and Dy780 (Dyomics); DyLight547, and/or DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source).

Calibration for Concentration Mapping

The systems and methods described herein allow in vivo quantification of fluorescent agents in an animal subject. The systems can accurately reconstruct the concentration of fluorescent agents as a function of location within the animal subject. Numerical computation of the distribution of fluorescent agents produces results that are dependent on the photochemical properties of the fluorescent agents as conjugated with biologically relevant probes. Specifically, the product of the quantum yield and absorption cross-section, or extinction coefficient, are included as numerical factors in the computational result, thereby masking the actual fluorochrome concentration. A priori estimation of these photochemical properties from first principles and application of such estimates to a tomographic reconstruction of in vivo fluorescence is unreliable and prone to error. Thus, there is a need for a method to account for these photochemical properties empirically and in vivo, in order to yield accurate quantification and allocation of fluorescent agent concentration.

The calibration method enables accurate quantification of FMT tomographic reconstructions of the distribution of fluorescent agent. The method involves the measurement by FMT, with the waveguiding-compensated tomographic reconstruction disclosed herein, of a known amount of fluorescent agent in solution (for example VivoTag680 or VivoTag750, VisEn Medical, Woburn, Mass.), injected into a phantom. This phantom can either be a synthetic material designed to match the optical properties of animal tissue and containing a cavity designed to hold the fluorescent agent, or it can be a container holding fluorescent agent that is in turn placed inside an animal cadaver. Phantom material may, for example, consist of an optically clear polyester resin (TAP Plastics, Dublin, Calif.) with a dispersion of Titanium Dioxide (TiO2, Sigma-Aldrich, St. Louis, Mo.) and ink to adjust the optical scattering and optical absorption properties of the phantom to those of biological tissue. Phantoms may be molded, machined or fabricated to any desired geometry or aspect ratio. In one embodiment, phantoms are molded to dimensions representative of small animal anatomies (such as thicknesses spanning a range of 13-25 mm) and machined with internal hollow cavities to accommodate fluorescent agents with dimensions representative of disease-related lesions in various animal models (such as tumor sizes in the range of 50-500 □L). These hollow cavities may be located at depths representative of various disease manifestations, from close to the surface (for subcutaneous disease models) to full depth within the phantom. The concentration of fluorescent agent in solution is measured in vitro, for example using spectrophotometry instrumentation such as the devices provided by Varian (Palo Alto, Calif.), before dispensing a known volume of the solution into the phantom. A complete FMT dataset of the phantom is then acquired, and the raw data are tomographically reconstructed. A region of interest (ROI) analysis is performed on the reconstructed distribution of fluorescent agent. The values in this ROI are then numerically scaled to match the known amount of fluorescent agent that had been dispensed into the phantom. Finally, this scale factor is applied to future reconstructions to convert the raw result of the tomographic reconstruction into a physically meaningful concentration of fluorescent agent. Scale factors can be generated to account for the photochemical properties of different fluorescent agents, such as ProSense680, OsteoSense750 and others (VisEn Medical, Woburn, Mass.). This calibration process may be repeated several times per agent to increase the statistical robustness of the calibration and decrease the impact of operator variability, batch to batch agent variability, and other sources of error. It is also possible to generate a single, scalar scale factor or a scale factor function mapping to an entire range of concentrations, as appropriate. The scale factor may also be a function of depth within the subject being scanned or of other physical properties of the subject. These functional scale factors may also be combined to produce a scale factor function with multiple parameters.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A method for compensating an image for waveguiding effects, the method comprising:
    (a) detecting excitation light emanating from at least part of a heterogeneous diffuse object at one or more wavelengths, thereby acquiring an intrinsic image;
    (b) detecting emission light emanating from at least part of said heterogeneous diffuse object at one or more wavelengths, thereby acquiring a detected emission image, said emission light emitted by an imaging probe located within or on said heterogeneous diffuse object as a result of excitation by said excitation light;
    (c) creating an estimated emission image using at least said intrinsic image;
    (d) determining a coincidence mask from said intrinsic image and said detected emission image; and
    (e) altering said detected emission image using at least said estimated emission image, thereby compensating said detected emission image for waveguiding effects.

2. The method of claim 1, wherein each of step (a) and step (b) comprises detecting light transmitted through at least part of said heterogeneous diffuse object.

3. The method of claim 1, wherein said heterogeneous diffuse object is a mammal.

4. The method of claim 1, wherein said heterogeneous diffuse object comprises biological tissue.

5. The method of claim 1, wherein said heterogeneous diffuse object is transilluminated with excitation light.

6. The method of claim 1, wherein said heterogeneous diffuse object is epi-illuminated with said excitation light.

7. The method of claim 1, wherein said excitation light detected in step (a) comprises near-infrared light.

8. The method of claim 1, wherein said emission light comprises fluorescent light emitted by said probe.

9. The method of claim 1, wherein step (c) comprises applying a statistical estimator to said intrinsic image to create said estimated emission image.

10. The method of claim 1, wherein step (e) comprises subtracting said estimated emission image from said detected emission image.

11. The method of claim 1, wherein step (e) comprises subtracting said estimated emission image from said detected emission image to obtain a residual image, and applying said coincidence mask to said residual image to obtain said waveguiding-compensated emission image.

12. The method of claim 1, wherein said intrinsic image and said detected emission image are 2-D images or are used in tomographic reconstruction to obtain a tomographic image.

13. The method of claim 1, further comprising repeating steps (a)-(e) to obtain a plurality of emission images compensated for waveguiding effects.

14. The method of claim 13, wherein said plurality of waveguiding-compensated emission images is used in tomographic reconstruction to obtain one or more tomographic images.

15. The method of claim 13, comprising determining a Born ratio from one or more of said waveguiding-compensated emission images and further masking said one or more waveguiding-compensated emission images.

16. The method of claim 1, wherein said probe is a near-IR probe.

17. A method of imaging a region within an object, the method comprising:
(a) administering to said object a probe comprising a fluorophore;
(b) directing excitation light into and/or onto said object at multiple locations;
(c) detecting excitation light emanating from or transmitted through at least part of said object, thereby acquiring an intrinsic image;
(d) detecting fluorescent light emitted from said probe within or on a surface of said object, thereby acquiring a detected emission image; and
(e) processing data from said intrinsic image and said detected emission image to provide a representation of said region within said object, said representation compensated for waveguiding effects, wherein step (e) comprises:
(i) creating an estimated emission image using at least said intrinsic image and altering said detected emission image using at least said estimated emission image; and
(ii) determining a coincidence mask from said intrinsic image and said detected emission image and altering said detected emission image using at least said coincidence mask.

18. The method of claim 17, wherein step (e) comprises determining a concentration or concentration map of said probe using calibration measurements of a phantom of said object.

19. A fluorescence molecular tomography imaging system comprising:
an excitation light source;
an optical imaging chamber configured to direct excitation light from said excitation light source into an object disposed within said chamber at multiple locations;
a detector configured to detect at multiple locations excitation light emanating from said object, thereby acquiring an intrinsic image, and fluorescent light emitted from one or more probes within or on a surface of said object, thereby acquiring a detected emission image;
a processor; and
a memory having instructions stored thereon, wherein the instructions, when executed by the processor, cause the processor to:
(i) create an estimated emission image using at least said intrinsic image,
(ii) alter said detected emission image using at least said estimated emission image,
(iii) determine a coincidence mask from said intrinsic image and said detected emission image, and
(iv) alter said detected emission image using at least said coincidence mask.

* * * * *

UNITED STATES PATENT AND TRADEMARK OFFICE
CERTIFICATE OF CORRECTION

PATENT NO. : 8,492,734 B2
APPLICATION NO. : 12/738615
DATED : July 23, 2013
INVENTOR(S) : Yared et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 561 days.

Signed and Sealed this
Thirtieth Day of December, 2014

Michelle K. Lee
*Deputy Director of the United States Patent and Trademark Office*